US00PP33892P2

(12) United States Plant Patent
Randag

(10) Patent No.: US PP33,892 P2
(45) Date of Patent: Jan. 18, 2022

(54) CALLA LILY PLANT NAMED 'DOZANALAS'

(50) Latin Name: *Zantedeschia sprengeri*
Varietal Denomination: Dozanalas

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/313,116

(22) Filed: May 6, 2021

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 6/10
See application file for complete search history.

(56) References Cited

PUBLICATIONS

UPOV hit on calla lily plant named, 'Dozanalas', QZ PBR 20202099, filed Sep. 5, 2020.*

* cited by examiner

*Primary Examiner* — Anne Marie Grunberg
(74) *Attorney, Agent, or Firm* — The Webb Law Firm

(57) ABSTRACT

'Dozanalas' is a new variety of calla lily plant having white colored spathes without a throat spot that produces 7-10 inflorescences per approximately 20 cm tuber. The flower stems are about 29-35 cm in height. The leaves are brownish green without maculations present and a smooth texture.

2 Drawing Sheets

Botanical classification: *Zantedeschia sprengeri*.
Varietal denomination: 'Dozanalas'.

BACKGROUND OF THE NEW PLANT

The present invention comprises a new and distinct variety of calla lily, botanically known as *Zantedeschia sprengeri* and hereinafter referred to by the varietal name 'Dozanalas'. 'Dozanalas' is a product of a planned breeding program, which had the objective of creating *Zantedeschia* hybrids for pot flower production in a wide range of colors with a classic flower shape. The new cultivar is a seedling selected from the crossing of *Zantedeschia sprengeri* variety 'Helvetia' (female parent, U.S. Plant Pat. No. 28,873) with *Zantedeschia sprengeri* variety 'Calgary' (male parent, U.S. Plant Pat. No. 24,275). 'Dozanalas' was selected in 2012 by the inventor in 't Zand, The Netherlands as one flowering plant within the progeny of the stated cross.

The first act of asexual reproduction of 'Dozanalas' by tissue culture was performed by the inventor in January of 2016 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants at approximately 8 weeks from planting directly in the soil in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozanalas' which, in combination, distinguish this calla lily as a new and distinct cultivar:

1. Medium white colored spathes without a throat spot;
2. Brownish green colored leaves; and
3. No leaf maculations present.

The new variety is similar to its female parent in the following traits: white spathe color without a throat spot, spathe width and length, green peduncle color, and the absence of leaf maculations. However, 'Dozanalas' exhibits a stronger flower curve than its female parent. Further, its female parent has a yellow/red spadix color and oval shaped leaves. The new variety is similar to its male parent in the following traits: white spathe color, spathe width and length, strong flower curve, and green peduncle color. However, its male parent exhibits a spathe throat spot, a yellow/red spadix color, oval shaped leaves, and the presence of leaf maculations.

When compared to calla lily plant named 'Diva Siberia' (U.S. Plant Pat. No. 32,492), both varieties exhibit white colored spathes without a throat spot and the absence of leaf maculations, but 'Diva Siberia' is a variety of *Zantedeschia aethiopica*, is much larger in stem height and spathe size than 'Dozanalas', and exhibits a sagittate leaf shape.

BRIEF DESCRIPTION OF THE DRAWINGS

The accompanying photographic drawings illustrate the new variety taken at approximately 8 weeks of age, with the colors being as nearly true as is possible with color illustrations of this type.

DESCRIPTION OF THE NEW PLANT

Figure 1:
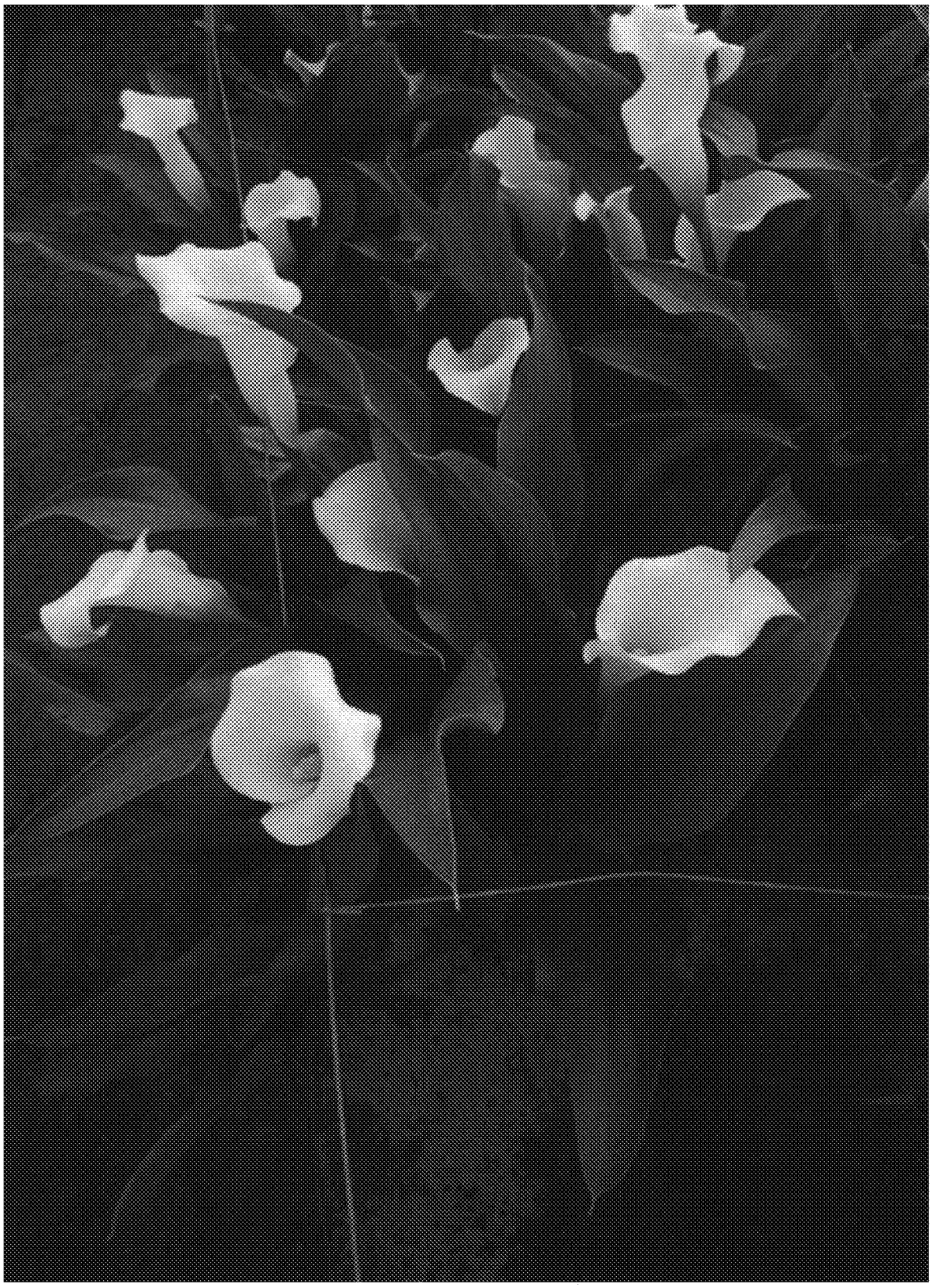
FIG. 1 is a close-up view of multiple flowering plants of the new variety.
Figure 2:
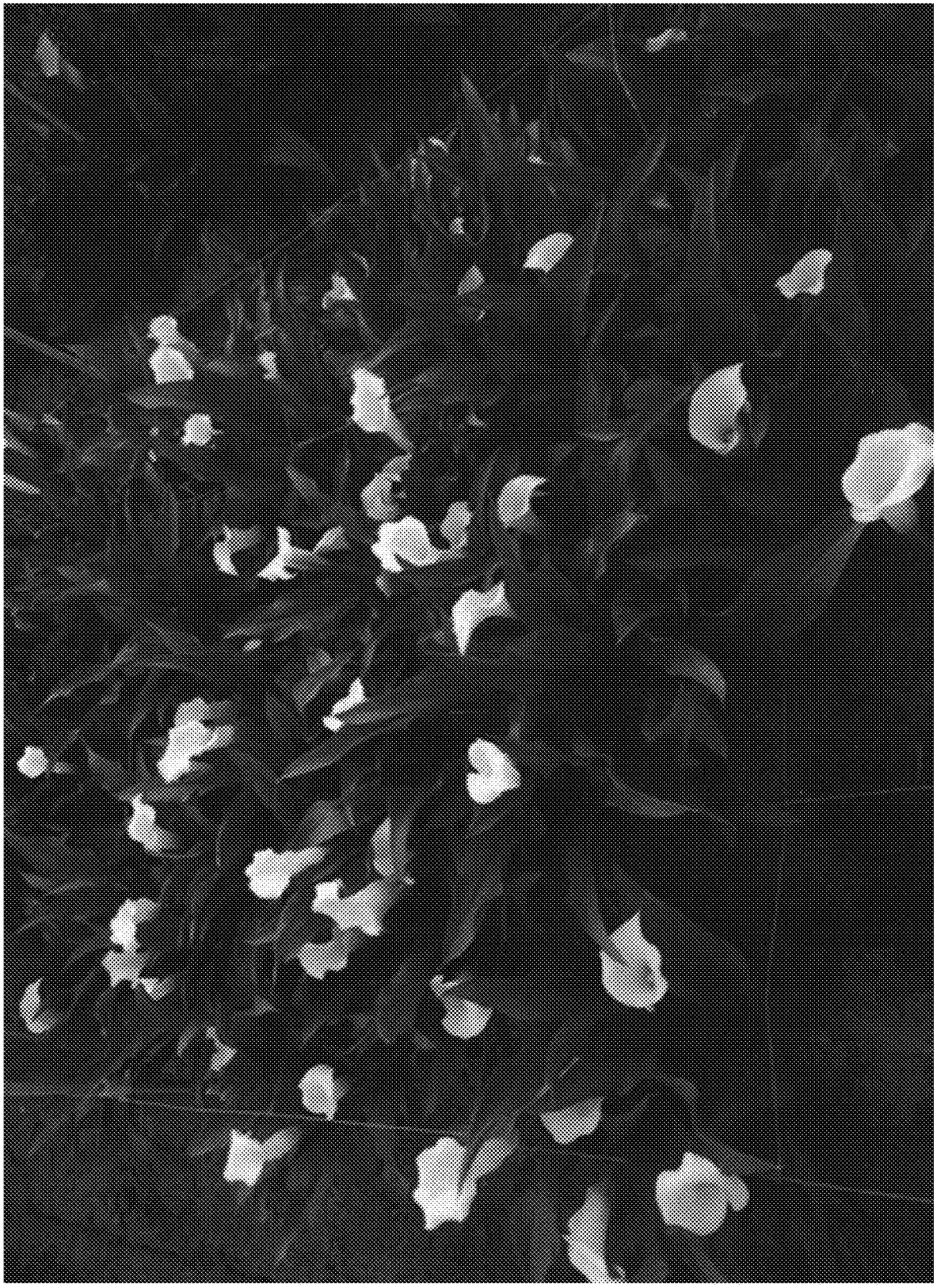
FIG. 2 illustrates multiple flowering plants of the new variety.

Type: Deciduous.

*Size*.—Height of the leaf canopy above the soil: 19-23 cm. Height of top of inflorescences above the soil: 29-35 cm. Diameter: 30-42 cm.

*Form*.—Semi-spreading.

*Number of inflorescences per tuber*.—Size approximately 20 cm in diameter: 7-10 inflorescences.

*Branches*.—Number: Average. Color: Yellow-Green Group RHS 145B to 145C. Young shoot color: Yellow-Green Group RHS 145A to 145B.

Leaves:

*Size*.—Width: 6-8 cm, with the broadest part being in the middle. Length: 21-26 cm.

*Number per plant*.—31-47.

*Leaf blade lobes*.—Absent.

*Shape*.—Lanceolate.

*Apex*.—Apiculate.

*Base*.—Attenuate.

*Margin*.—Entire; having a color of Green Group RHS 137B to 137C.

*Color*.—Upper surface: Green Group RHS 137B to 137C, with no maculations present. Lower surface: Yellow-Green Group RHS 147B to 147C, with no maculations present.

*Veins*.—Configuration: Pinnate. Color: Yellow-Green Group RHS 146C to 146D.

*Surface texture*.—Smooth (both surfaces).

*Petiole*.—Length: 19-25 cm. Diameter: 5-8 mm. Color: The base is Yellow-Green Group RHS 144B to 144C, the upper part is Yellow-Green Group RHS 146A to 146B.

Roots:

*Color*.—White Group RHS 155C.

*Branching description*.—Fibrous root system. Several main roots emerge from the top of the tuber and form a small number of lateral roots.

Spathe:

*Size*.—Length (measured from opening to tip): 5-7.5 cm. Width: 4-6 cm. Height: 6-9 cm.

*Color*.—Throat spot: Absent. Upper surface: White Group RHS 155A to 155B. Lower surface: White Group RHS 155C to 155D. Vein color: Yellow-Green Group RHS 145B to 145C.

*Shape*.—Leaf-like.

*Apex*.—Caudate.

*Base*.—Amplexicaul.

*Margin*.—Entire, with a color of White Group RHS 155A to 155B.

Spadix:

*Shape*.—Cylinder.

*Size*.—Length: 30-43 mm. Diameter: 4-5 mm.

*Color*.—Yellow Group RHS 7B to 7C.

*Position relative to spathe*.—Upright.

Peduncle:

*Size*.—Length: 31-35 cm. Diameter: 5-7 mm.

*Color*.—The upper part is Yellow-Green Group RHS 144A to 144B, the lower part is Yellow-Green Group RHS 144C to 144D.

*Texture*.—Smooth.

Reproductive organs:

*Location of female organs*.—Basal position of the spadix.

*Location of male organs*.—Upper position of the spadix.

*Perianth*.—Conspicuous.

*Stamens*.—Presence: Not visible before pollen release. Number: Between 480 and 600. Pollen amount: Scarce. Color: Between White Group RHS 155B and 155C.

*Anther*.—Shape: Round. Length: Less than 1 mm. Color: Yellow Group RHS 8B to 8C.

*Filament*.—Length: Less than 1 mm. Color: White Group RHS 155D.

*Pistils*.—Number: 15 to 30. Length beyond perianth: About 1 mm.

*Stigma*.—Shape: Round. Size: Less than 1 mm.

*Style*.—Length: Less than 1 mm. Color: Yellow Group RHS 8B to 8C.

*Ovaries*.—Texture: Smooth. Length: Between 1 to 10 mm. Width: Between 1 to 10 mm. Color: The top color is Yellow Group RHS 2B to 2C, the bottom color is Yellow-Green Group RHS 150B to 150C.

Seeds:

*Length*.—2.5-3.9 mm.

*Width*.—1.8-2.4 mm.

*Color*.—Yellow-Green Group RHS 152C to 152D.

*Amount*.—8 per inflorescence.

Disease resistance: No unusual susceptibility/resistance to diseases noticed to date.

Pest resistance: No unusual susceptibility/resistance to pests noticed to date.

Heat tolerance: No heat tolerance.

Hardiness: Not tested to date.

Flowering: In general, the time from indoor and outdoor planting to first flowering takes about eight weeks in The Netherlands.

Lastingness: About two weeks on the plant.

Fragrance: None.

I claim:

1. A new and distinct variety of calla lily plant named 'Dozanalas' as herein described and illustrated.

* * * * *